US010167442B1

(12) United States Patent
Al Sayegh

(10) Patent No.: US 10,167,442 B1
(45) Date of Patent: Jan. 1, 2019

(54) COMPOSITION FOR CLEANING DISARTICULATED SKELETONS

(71) Applicant: Husain A. A. Al Sayegh, Safat (KW)

(72) Inventor: Husain A. A. Al Sayegh, Safat (KW)

(*) Notice: Subject to any disclaimer, the term of this patent is extended or adjusted under 35 U.S.C. 154(b) by 0 days.

(21) Appl. No.: 16/101,362

(22) Filed: Aug. 10, 2018

(51) Int. Cl.
| | |
|---|---|
| C11D 3/02 | (2006.01) |
| C11D 3/39 | (2006.01) |
| C11D 3/395 | (2006.01) |
| C11D 7/18 | (2006.01) |
| B08B 3/08 | (2006.01) |
| B08B 3/10 | (2006.01) |
| B08B 5/00 | (2006.01) |
| C11D 7/04 | (2006.01) |
| A61L 2/18 | (2006.01) |
| B08B 3/04 | (2006.01) |
| C11D 3/30 | (2006.01) |
| C11D 7/26 | (2006.01) |
| C11D 7/32 | (2006.01) |
| B08B 7/00 | (2006.01) |
| C11D 3/04 | (2006.01) |
| C11D 11/00 | (2006.01) |

(52) U.S. Cl.
CPC ............ *C11D 7/04* (2013.01); *A61L 2/183* (2013.01); *B08B 3/04* (2013.01); *B08B 3/042* (2013.01); *B08B 3/044* (2013.01); *B08B 3/08* (2013.01); *B08B 3/10* (2013.01); *B08B 5/00* (2013.01); *B08B 7/0021* (2013.01); *C11D 3/044* (2013.01); *C11D 3/30* (2013.01); *C11D 3/3902* (2013.01); *C11D 3/3942* (2013.01); *C11D 3/3947* (2013.01); *C11D 7/26* (2013.01); *C11D 7/3209* (2013.01); *A61L 2202/20* (2013.01); *C11D 11/0052* (2013.01)

(58) Field of Classification Search
CPC ......... C11D 3/044; C11D 3/30; C11D 3/3902; C11D 3/3942; C11D 3/3947; C11D 7/3209; C11D 7/26; B08B 3/04; B08B 3/042; B08B 3/044; B08B 5/00; B08B 7/0021; B08B 3/08; B08B 3/10
USPC ............. 510/365, 372, 499, 505; 134/22.12, 134/22.13, 22.19, 26, 34, 36
See application file for complete search history.

(56) References Cited

U.S. PATENT DOCUMENTS 5,044,960 A 9/1991 De Porteous

FOREIGN PATENT DOCUMENTS

ES 2042416 A1 12/1993

OTHER PUBLICATIONS

"Cleaning Bones", Nawrocki, University of Indianapolis Archeology & Forensics Laboratory, p. 1-4, 1997. (Year: 1997).*
Zarrelli, "The Lost and Found Art of Assembling Whale Skeletons," Atlas Obscura, Nov. 4, 2015; printed from https://www.atlasobscura.com/articles/the-lost-and-found-art-of-assembling-whale-skeletons.
National Park Service, "Whale 68: Cleaning and Preparation", Apr. 14, 2015; printed from https://www.nps.gov/glba/learn/nature/cleaning-and-preparation.htm.
"About Bone Building: Animal Skeleton/Bones Cleaning and Assembly"; printed from https://www.theboneman.com/aboutbonebuilding.html on Jul. 31, 2018.
Holden, "A Method of Cleaning Skulls and Disarticulated Skeletons", The Condor (1914), vol. XVI, pp. 239-241.
Ososky, "History of Collecing, Preparing and Degreasing Whale Skeletons at the Smithsonian Institution" (2012), 8 pages, printed from www.museum.nantes.fr/pages/21_activitesscientifiques/TableRonde_squelettes_fevrier2012/PDF/J.%20Ososky%20-%20History%20od%20Collecting,%20Preparing%20...%20Smithsonian%20Institution.pdf.
Aboe, "We are not alone and not the first!", (2013), 7 pages, printed from onceinawhale.com/2013/07/02/we-are-not-alone-and-not-the-first on Aug. 17, 2018.

* cited by examiner

*Primary Examiner* — Gregory R Delcotto
(74) *Attorney, Agent, or Firm* — Richard C. Litman

(57) ABSTRACT

The composition for cleaning disarticulated skeletons is a mixture of ammonia, hydrogen peroxide and water. The composition may further include ozone continuously pumped into the mixture while soaking the skeleton. The skeleton may initially be soaked in a composition having 7% ammonia by volume and 8-10% hydrogen peroxide by volume, the balance being water, e.g., for a period of ten days. The composition may be maintained at 20° C. and ozone may be continuously pumped during the ten-day period. If any grease remains, the bones may be soaked again, e.g., in a composition having 3% ammonia and 3% hydrogen peroxide for an additional seven days, again with continuous pumping of ozone at a rate of 200 mg/hr into the mixture, followed by rinsing with water and drying.

7 Claims, No Drawings

COMPOSITION FOR CLEANING DISARTICULATED SKELETONS

BACKGROUND

1. Field

The disclosure of the present patent application relates to processing animal skeletons for display in museums and the like, and particularly to a composition for cleaning disarticulated skeletons, especially whales, to degrease and whiten the bones and to remove the lingering odor of decaying organic material.

2. Description of the Related Art

For purposes of study and display, animal bones must first be carefully cleaned and prepared. The first step in such preparation is the removal of soft tissue, typically through maceration. A basic method of maceration involves simply placing the bones in water and allowing natural bacteria to remove the tissue. However, since this can be time consuming, as well as odoriferous, a commonly used method for removing soft tissue from bones involves the use of biological cleaning powders or enzyme stain removing powders, such as conventional detergent powders.

Following the removal of the soft tissue, the fatty oils must be removed from the bones. A basic method for removal of the fatty oils is to simply soak the bones in soapy water for about 12 hours. Depending on the type(s) and quantity of oil, this process may have to be repeated numerous times. Once the fatty oils no longer appear during the soak, the bones may finally be cleaned via soaking in an aqueous solution of hydrogen peroxide.

Although the above process is relatively common for the treatment and cleaning of small animal bones, it may not be effective for the preparation of larger animal bones, such as those of whales, which require particular care. A whale's bones may be porous, having small cavities for the storage of fatty acids. These deposits of fatty acids may decay over a period of several years, leaving a greasy coating that may discolor the bones and produce an odor of decaying organic matter, and in some cases, may produces acids that cause deterioration of the skeleton. Consequently, the skeleton, which often becomes disarticulated in the process of recovering, transporting, storing, and processing the remains, should be thoroughly cleaned for display, including bleaching the bones to improve their color or appearance. Thus, a composition for cleaning disarticulated skeletons solving the aforementioned problems is desired.

SUMMARY

The composition for cleaning disarticulated skeletons is a mixture of ammonia, hydrogen peroxide and water. The composition may further include ozone continuously pumped into the mixture while soaking the skeleton. The skeleton may initially be soaked in a composition having 7% ammonia by volume and 8-10% hydrogen peroxide by volume, the balance being water, e.g., for a period of ten days. The composition may be maintained at 20° C. and ozone at an approximate rate of 200 mg/hr may be continuously pumped during the ten-day period. If any grease remains, the bones may be soaked again, e.g., in a composition having 3% ammonia and 3% hydrogen peroxide for an additional seven days, again with continuous pumping of ozone at an approximate rate of 200 mg/hr into the mixture, followed by rinsing with water and drying.

These and other features of the present disclosure will become readily apparent upon further review of the following specification.

DETAILED DESCRIPTION OF THE PREFERRED EMBODIMENTS

The composition for cleaning disarticulated skeletons is a mixture of ammonia, hydrogen peroxide and water. The composition may further include ozone continuously pumped into the mixture while soaking the skeleton. The skeleton may initially be soaked in a composition having 7% ammonia by volume and 8-10% hydrogen peroxide by volume, the balance being water, e.g., for a period of ten days. The composition may be maintained at 20° C. and ozone at an approximate rate of 200 mg/hr may be continuously pumped during the ten-day period. If any grease remains, the bones may be soaked again, e.g., in a composition having 3% ammonia and 3% hydrogen peroxide for an additional seven days, again with continuous pumping of ozone at an approximate rate of 200 mg/hr into the mixture, followed by rinsing with water and drying.

The composition and the procedure for using the composition will be better understood by reference to the following examples. Three female Bryde's whales were found dead in Kuwait waters between 2012 and 2015. The first dead whale was dissected on site and the bones and flesh were buried separately. The latter two whales were transported near laboratory facilities and temporarily buried in marked areas. Periodic inspection showed some mummification beginning to occur together with some dissolution of the bones (thought to be due to the buildup of acids), so that a decision was made to extract and preserve the bones with a view towards articulating the skeletons. After some trial and error, the following procedure was found to be most successful.

The skeletons were carefully excavated and the bones were gently removed, in one case with the assistance of a water tanker to wash away the soil without disturbing the bones. The bones were collected and scraped clean of soil and remaining flesh as best as possible. The bones were piled into a 3,000 liter water tank, which was filled with water and Vircon S (a commercial disinfectant) at 4-7% and allowed to sterilize for 48 hours. Then, the water was drained from the tank, and the bones were removed and pressure washed with a ¼ hp pressure washer, taking care not to damage the bones. Any remaining flesh was cut away with knives and hatchet, and the bones were placed back in the tank for degreasing.

The tank was filled with a composition of water, ammonia and hydrogen peroxide. The concentration of the ammonia in the composition was 7% by volume, and the concentration of the hydrogen peroxide in the composition was between 8% and 10% by volume. The water is preferably maintained at a temperature of about 20° C. Ozone was continuously circulated through the composition at an approximate rate of 200 mg/hr as the bones were left to soak. The tank was covered with a tarp. A circulation pump was placed in the tank to continuously circulate the composition, and the bones were left to soak for ten days. Additional hydrogen peroxide (about 0.05% by volume) was added every three days.

Following the ten day soaking period, the bones were removed from the tank and rinsed, first with water supplied by a hose, and then via soaking in fresh water. The process was then repeated but in a similar composition with an ammonia concentration of 3% by volume and a hydrogen peroxide concentration of 3% by volume. This secondary soaking was performed for a period of seven days. The ozone and circulation pump were also left on.

Following the secondary soaking, the bones were removed from the tank, and then soaked in fresh water for 24 hours. The bones were then dried in direct sunlight, with additional periods of rinsing in rain. Initially, the prepared whale bones appeared yellow, with a faint odor, but, as they dried, the odor faded and the bones became white (a brilliant pearl color). Drying by exposure to the elements preferably took place in 34-40° C. heat for a week.

After this process of cleaning and degreasing the bones, a long process of repairing the bones and articulating the skeletons took place.

It is to be understood that the composition for cleaning disarticulated skeletons is not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

I claim:

1. A method of cleaning a disarticulated skeleton, comprising the steps of:
    placing bones from the skeleton in a tank;
    filling the tank with a mixture of water, ammonia and hydrogen peroxide;
    soaking the bones in the tank filled with the mixture;
    continuously pumping ozone through the mixture in the tank while soaking the bones;
    removing the bones from the tank; and
    rinsing the bones.

2. The method of cleaning a disarticulated skeleton according to claim 1, wherein the mixture comprises:
    7% ammonia by volume; and
    between 8% and 10% hydrogen peroxide by volume, the balance being water.

3. The method of cleaning a disarticulated skeleton according to claim 2, wherein the step of soaking the bones in the composition and the ozone at a rate of 200 mg/hr is performed for a period of at least seven days.

4. The method of cleaning a disarticulated skeleton according to claim 2, further comprising the step of covering the tank while soaking the bones in the mixture.

5. The method of cleaning a disarticulated skeleton according to claim 2, further comprising the step of adding an additional 0.05% by volume of hydrogen peroxide to the mixture every three days.

6. The method of cleaning a disarticulated skeleton according to claim 2, further comprising the steps of:
    after the step of rinsing the bones, placing at least some of the bones of the skeleton back in the tank;
    filling the tank with a second mixture having 3% ammonia by volume and 3% hydrogen peroxide by volume, the balance being water;
    soaking the bones in the tank filled with the second mixture;
    continuously pumping ozone at a rate of 200 mg/hr through the second mixture in the tank while soaking the bones;
    removing the bones from the tank; and
    rinsing the bones.

7. The method of cleaning a disarticulated skeleton according to claim 2, further comprising the step of drying the skeleton in sunlight after the rinsing step.

* * * * *